(12) United States Patent
Boguslavsky et al.

(10) Patent No.: US 8,721,907 B2
(45) Date of Patent: May 13, 2014

(54) METHOD AND SYSTEM FOR MILLING AND IMAGING AN OBJECT

(75) Inventors: Dimitry Boguslavsky, Haifa (IL); Colin Smith, D.N. Menashe (IL)

(73) Assignee: Camtek Ltd., Migdal Haemek (IL)

( * ) Notice: Subject to any disclaimer, the term of this patent is extended or adjusted under 35 U.S.C. 154(b) by 217 days.

(21) Appl. No.: 13/282,492

(22) Filed: Oct. 27, 2011

(65) Prior Publication Data
US 2012/0103938 A1 May 3, 2012

Related U.S. Application Data

(60) Provisional application No. 61/408,609, filed on Oct. 31, 2010.

(51) Int. Cl.
*C23F 1/00* (2006.01)
(52) U.S. Cl.
USPC .................................. 216/59; 216/60; 216/66
(58) Field of Classification Search
USPC ............................................... 216/59, 60, 66
See application file for complete search history.

(56) References Cited

U.S. PATENT DOCUMENTS

| | | | |
|---|---|---|---|
| 7,423,263 B2 * | 9/2008 | Hong et al. | 250/304 |
| 2010/0197142 A1 * | 8/2010 | Randolph et al. | 438/710 |
| 2010/0243889 A1 * | 9/2010 | Faber et al. | 250/307 |
| 2011/0006207 A1 * | 1/2011 | Arjavac et al. | 250/307 |
| 2011/0017927 A1 * | 1/2011 | Zaykova-Feldman et al. | 250/559.01 |
| 2011/0031397 A1 * | 2/2011 | Zaykova-Feldman et al. | 250/307 |
| 2011/0117748 A1 * | 5/2011 | Chandler et al. | 438/710 |

* cited by examiner

*Primary Examiner* — Binh X Tran
(74) *Attorney, Agent, or Firm* — Oren Reches

(57) ABSTRACT

A system and a method for milling and inspecting an object. The method may include performing at least one iteration of a sequence that includes: milling, by a particle beam, a first surface of the object, during a first surface milling period; obtaining, by an electron detector, an image of a second surface of the object during at least a majority of the first surface milling period; wherein the object is expected to comprise an element of interest (EOI) that is positioned between the first and second surfaces; milling, by the particle beam, the second surface of the object during a second surface milling period; wherein each of the first surface milling period and the second surface milling period has a duration that exceeds a long duration threshold; obtaining by the electron detector an image of the first surface of the object during at least a majority of the second surface milling period.

13 Claims, 18 Drawing Sheets

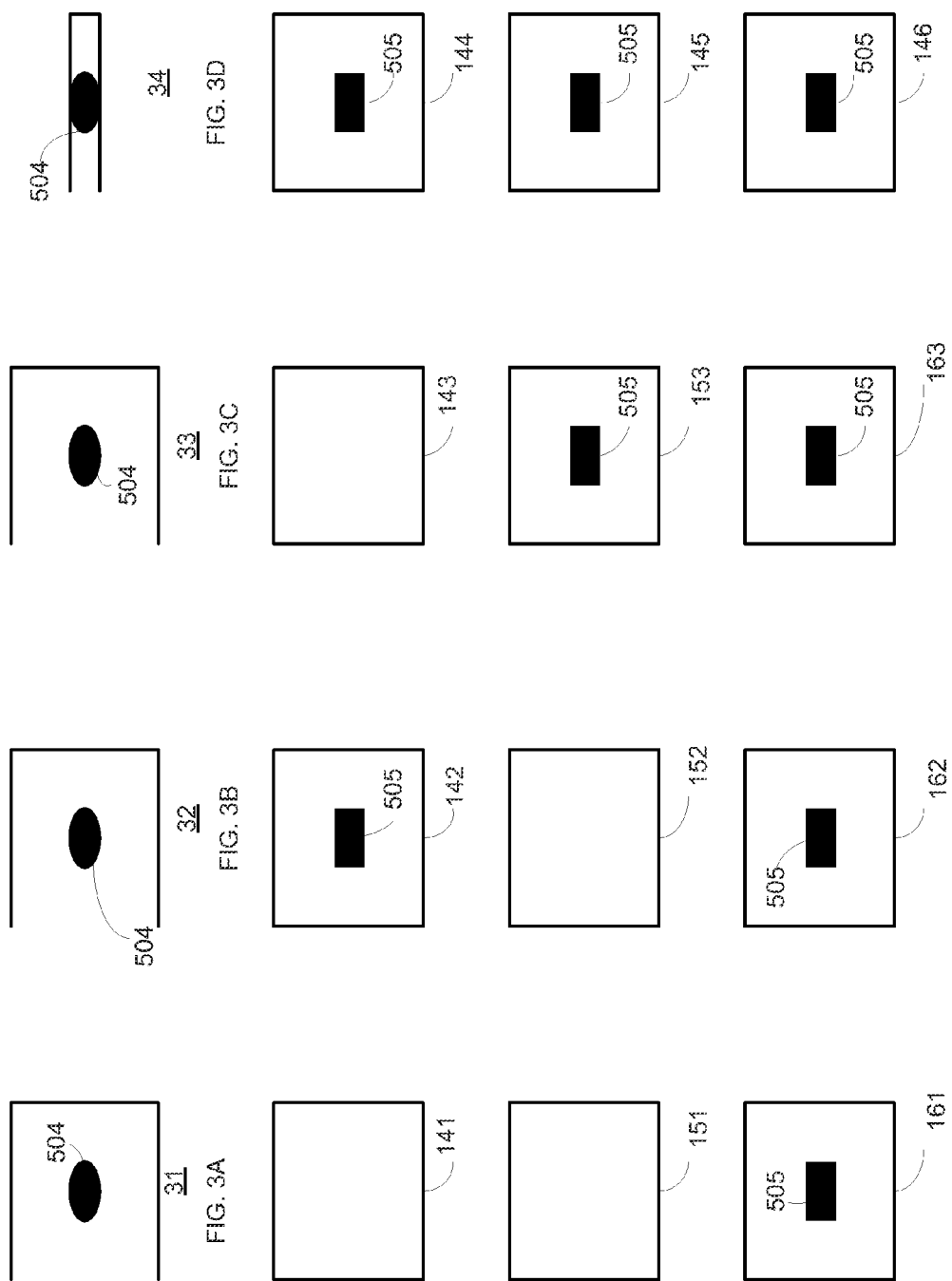

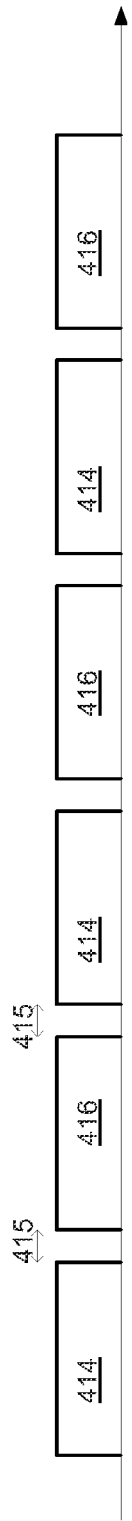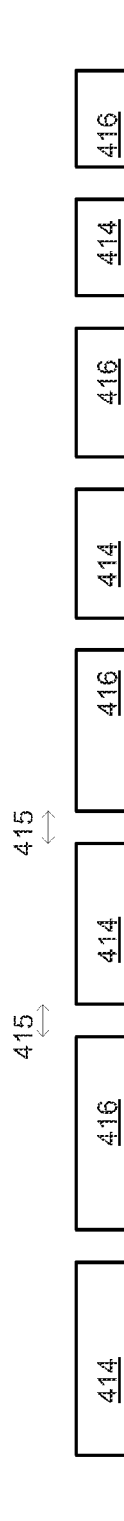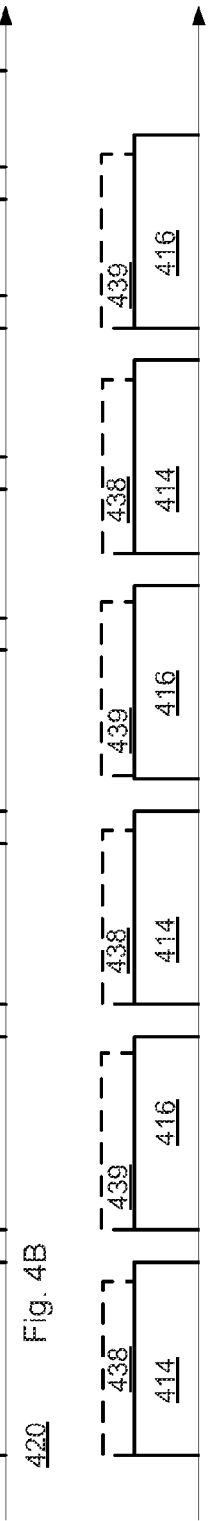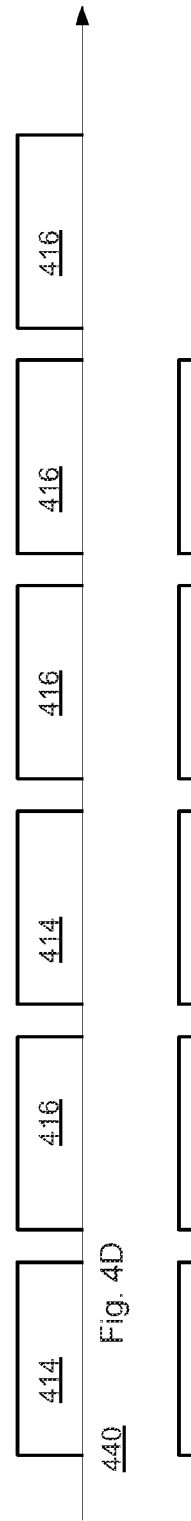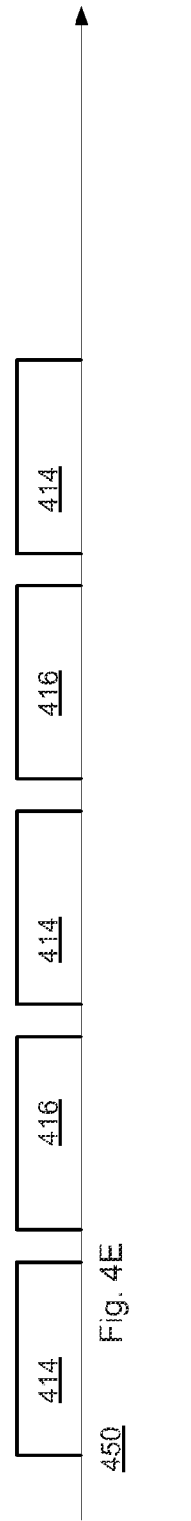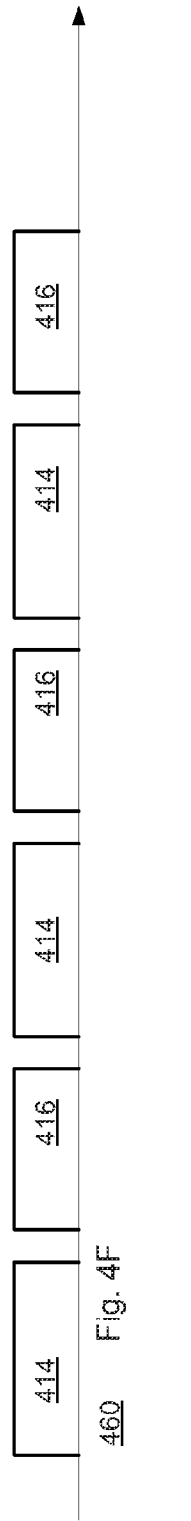

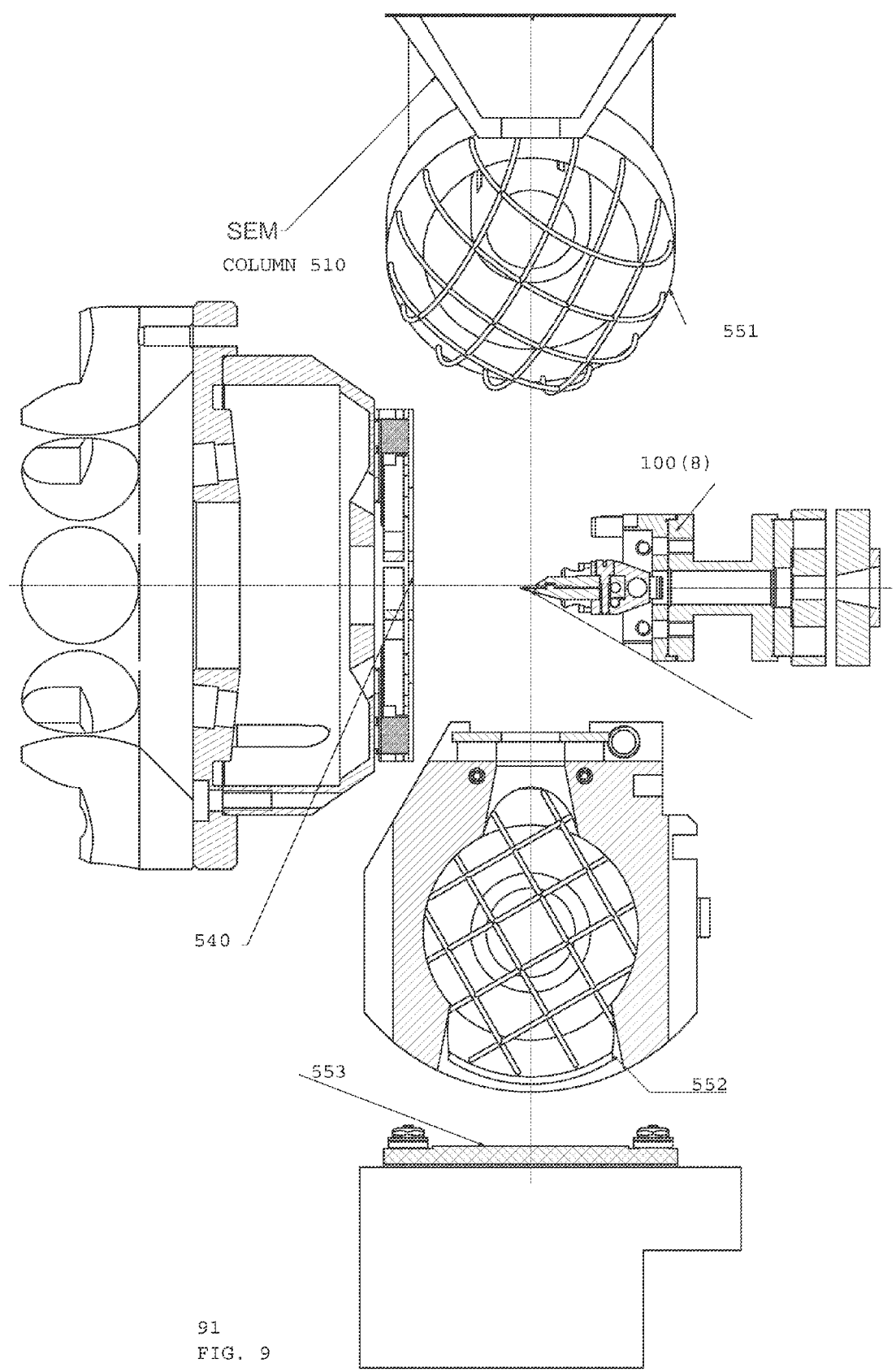

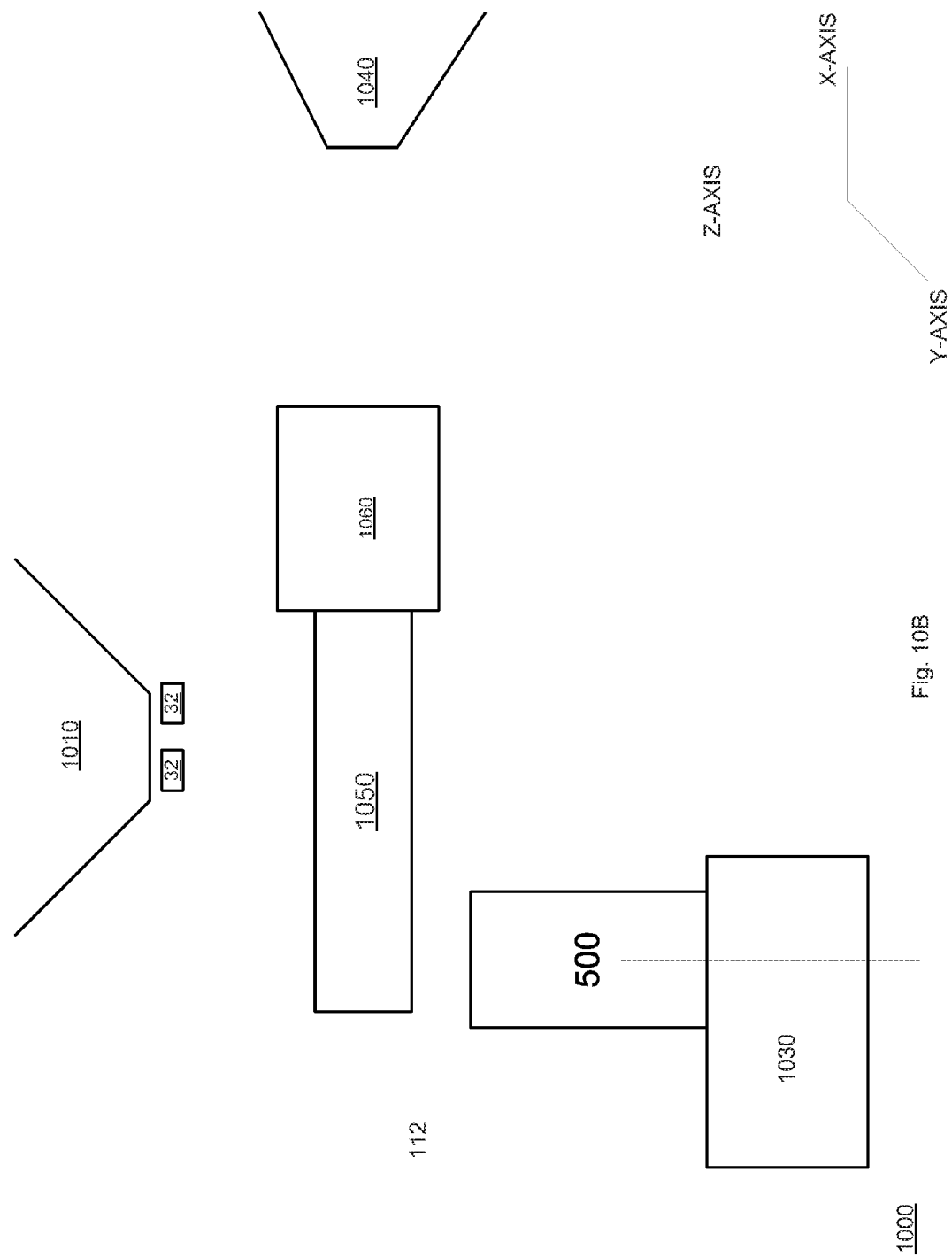

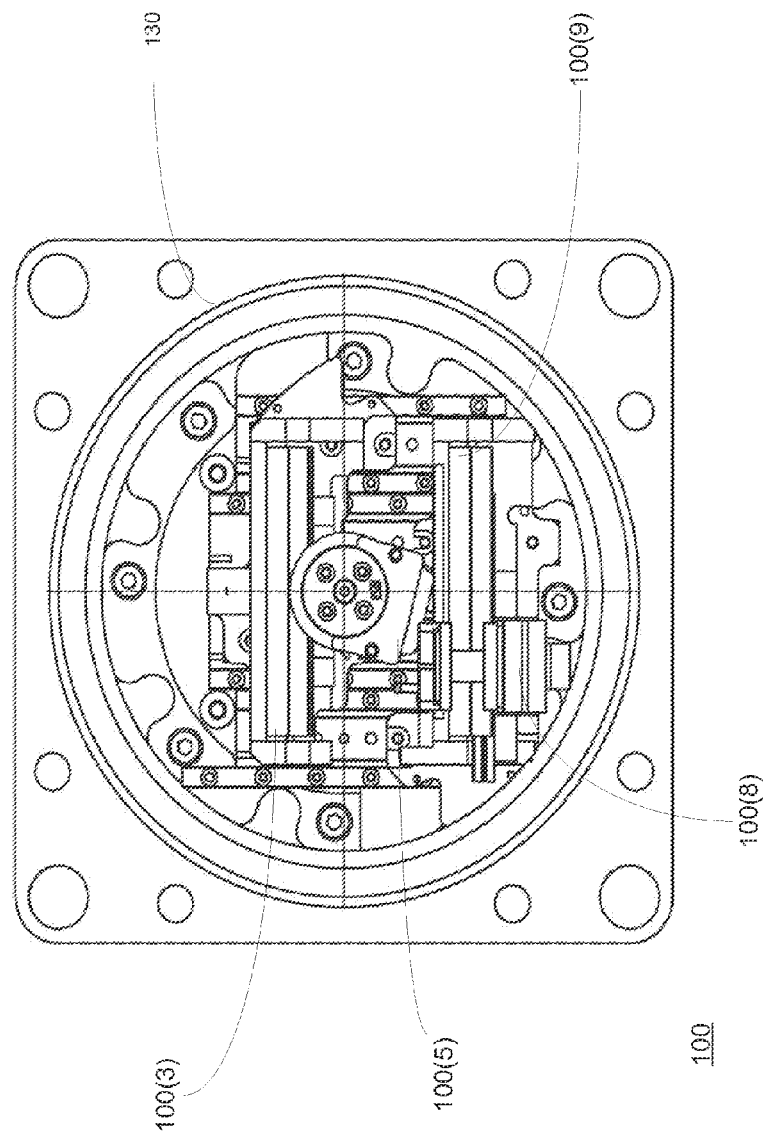

METHOD AND SYSTEM FOR MILLING AND IMAGING AN OBJECT

RELATED APPLICATIONS

The application claims the priority of U.S. provisional patent Ser. No. 61/408,609 filing date Oct. 31, 2010, which is incorporated herein by reference.

FIELD OF THE INVENTION

The invention relates to methods and systems for controlled milling.

BACKGROUND

There is a growing need to generate thinner samples for inspection. The preparation of samples should be fast and accurate.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

FIGS. 3a-3h illustrate various cross sections and various images according to an embodiment of the invention;

FIGS. 4a-4f are timing diagrams according to various embodiments of the invention;

FIG. 9 illustrates a portion of a system and an object according to an embodiment of the invention;

FIGS. 10A-10C illustrate a system and an object according to various embodiments of the invention;

FIGS. 11A-11D illustrate a manipulator of a system and an object according to various embodiments of the invention;

SUMMARY

Figure 1:
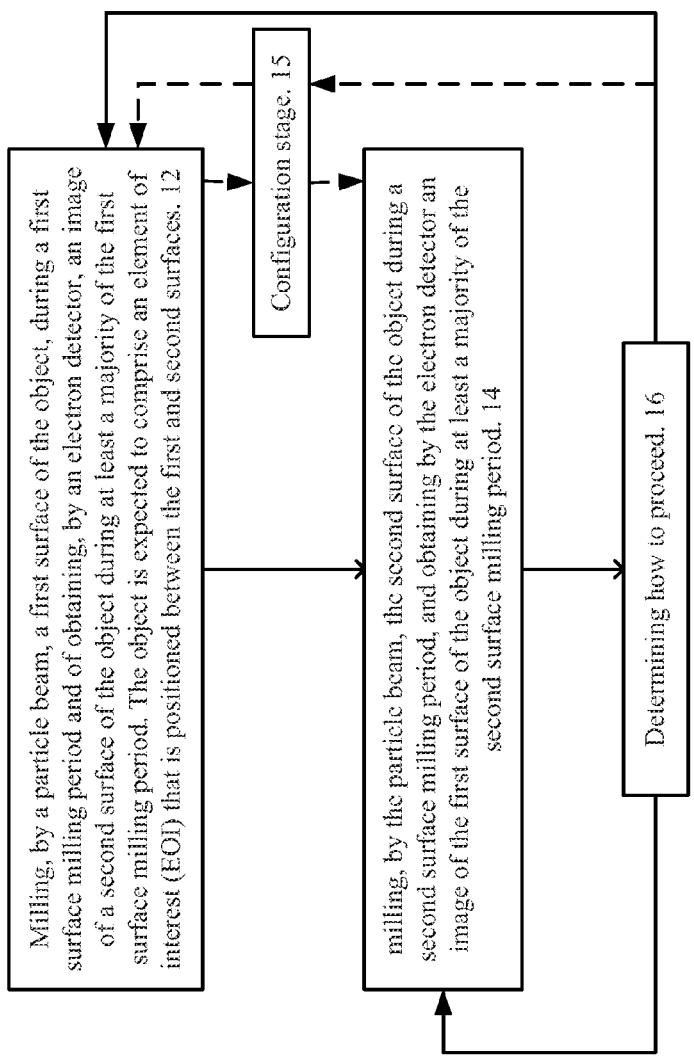
FIG. 1 illustrates a method according to an embodiment of the invention.

A system for milling and inspecting an object, the system may include a controller, an ion miller, an image processor, a first electron detector; wherein the system may be arranged to perform at least one iteration of a sequence that comprises: milling, by a particle beam from the ion miller, a first surface of the object, during a first surface milling period; obtaining, by the electron detector, an image of a second surface of the object during at least a majority of the first surface milling period; wherein the object is expected to comprise an element of interest (EOI) that is positioned between the first and second surfaces; milling, by the particle beam, the second surface of the object during a second surface milling period; wherein each of the first surface milling period and the second surface milling period has a duration that exceeds a long duration threshold; obtaining by the electron detector an image of the first surface of the object during at least a majority of the second surface milling period.

The controller may be arranged to stop the milling of the first surface and the milling of the second surface upon a detection, by the image processor, of pixels of the EOI in the image of the first surface and in the image of the second image.

The controller may be arranged to determine that the EOI has been exposed at the first and second surfaces; and to stop the milling of the first surface and the milling of the second surface.

The system may be arranged to perform multiple iterations of the sequence; wherein a length of at least one of the first and milling periods decreases with an expected decrement in a distance between the first and second surfaces.

The system may be arranged to perform multiple iterations of the sequence, wherein the ion miller may be arranged to reduce an energy of the particle beam with an expected decrement in a distance between the first and second surfaces.

The system may include a mechanical element that may be arranged to change a spatial relationship between the object and the changed particle device between the milling of the first surface of the object and milling the second surface of the object.

The system may include a transmissive image detector; wherein the image processor may be arranged to generate a transmissive image of the object based upon detection signals from the transmissive image detector.

The controller may be arranged to determine, based on the transmissive image of the object, whether the object may include the EOI and to stop an execution of the sequence of the first and second surfaces if the controller determines that the object does not comprise the EOI.

The controller may be arranged to determine whether the object may include the POI only after the transmissive image of the object exhibits a predetermined signal to noise ratio.

A method for milling and inspecting an object, the method may include performing at least one iteration of a sequence that comprises: (a) milling, by a particle beam, a first surface of the object, during a first surface milling period; (b) obtaining, by an electron detector, an image of a second surface of the object during at least a majority of the first surface milling period; wherein the object is expected to comprise an element of interest (EOI) that is positioned between the first and second surfaces; (c) milling, by the particle beam, the second surface of the object during a second surface milling period; wherein each of the first surface milling period and the second surface milling period has a duration that exceeds a long duration threshold; and (d) obtaining by the electron detector an image of the first surface of the object during at least a majority of the second surface milling period.

The method may include stopping the milling of the first surface and the milling of the second surface upon a detection of pixels of the EOI in the image of the first surface and in the image of the second surface.

The method may include determining that the EOI has been exposed at the first and second surfaced; and stopping the milling of the first surface and the milling of the second surface.

The method may include performing multiple iterations of the sequence; wherein a length of at least one of the first and surface milling periods decreases with an expected decrement in a distance between the first and second surfaces.

The method may include performing multiple iterations of the sequence, wherein an energy of the particle beam reduces with an expected decrement in a distance between the first and second surfaces.

The particle beam may be generated by an ion miller. The method may include changing a spatial relationship between the object and the changed particle device between the milling of the first surface of the object and milling the second surface of the object.

The method may include comprising determining, based on a transmissive image of the, whether the object comprises the EOI and stopping an execution of the sequence of the first and second surfaces if determining that the object does not comprise the EOI.

The method may include determining whether the object comprises the POI only after the transmissive image of the object exhibits a predetermined signal to noise ratio.

The long duration threshold may exceed 0.1 seconds, one second, few seconds, half a minute and even more.

The duration of each of the first and second surface milling period may exceed a time gap between an end of a first surface milling period and a start of a second surface milling period.

The duration of each of the first and second surface milling period may be at least ten times a time gap between an end of a first surface milling period and a start of a second surface milling period.

DETAILED DESCRIPTION OF THE DRAWINGS

The foregoing and other objects, features, and advantages of the present invention will become more apparent from the following detailed description when taken in conjunction with the accompanying drawings. In the drawings, similar reference characters denote similar elements throughout the different views.

Because the illustrated embodiments of the present invention may for the most part, be implemented using electronic components and circuits known to those skilled in the art, details will not be explained in any greater extent than that considered necessary for the understanding and appreciation of the underlying concepts of the present invention and in order not to obfuscate or distract from the teachings of the present invention.

FIG. 1 illustrates a method 10 according to an embodiment of the invention.

Method 10 starts by stage 12 of milling, by a particle beam, a first surface of an object, during a first surface milling period and of obtaining, by an electron detector, an image of a second surface of the object during at least a majority of the first surface milling period.

The object is expected to comprise an element of interest (EOI) that is positioned between the first and second surfaces.

The EOI can be a defect, a foreign element, a crack, can be made of a material that differs from the material of the object that surrounds the EOI, and the like. The EOI can have different electron optics characters than the material that surrounds it. It can be, for example, less transparent to charged particle.

Stage 12 may be followed by stage 14 of milling, by the particle beam, the second surface of the object during a second surface milling period, and obtaining by the electron detector an image of the first surface of the object during at least a majority of the second surface milling period.

Each of the first surface milling period and the second surface milling period has a duration that exceeds a long duration threshold. The long duration threshold can be a fraction of a second, few seconds, a fraction of a minute and even more than a minute. The long duration threshold can be set based on required image quality—higher quality is obtained with longer image obtaining durations.

The duration of each of the first and second surface milling period may exceed a time gap between an end of one milling period and a start of a consecutive milling period.

The duration of each of the first and second surface milling period can be at least ten times, at least forty times, at least fifty times and even more the time gap between an end of a first surface milling period and a start of a second surface milling period.

Stages 12 and 14 can form a sequence of stages. Stage 14 may be followed by a control stage 16 of determining how to proceed:

a. Repeat stages 12 and 14 (repeat the sequence of stages),
b. Continue an execution of stage 12 alone.
c. Continue executing stage 14 alone.
d. Changing one or more characteristic of the milling process. The characteristic can be a length of a milling period, an energy of the particle beam, and the like.

Stage 16 may be followed by each one of stages 12 and 14, as illustrated by various lines that connect box 16 of FIG. 1 to boxes 12, 15 and 15.

As indicated above, the sequence can be repeated multiple times. Different iterations of the sequence can differ from each other by duration, energy of charged particle beam and other characters—as determined during control stage 16.

It is expected that as the method progresses (and the number of iteration increases) that the thickness of the object (and especially the distance between the first and second surfaces) will decrease and the milling iterations will be less aggressive—as the EOI is getting closer to the first or second surfaces. For example, the milling process can start at a distance of 100 nanometers and can end at a distance of about 20 nanometers.

Stage 16 can determine to stop the repetition of the sequence of stages 12 and 14 when the EOI is exposed. EOI can be regarded as exposed when a predetermined part of the EOI is exposed. This predetermined part can be of at least a predetermined size of shape.

It is noted that stage 12 can be continued (even if stage 14 is halted) when the EOI is exposed at the second surface. Additionally or alternatively, stage 14 can be stopped (even if stage 12 is halted) if the EOI is exposed at the first surface.

Stage 16 can include determining to stop the milling of the first surface and the milling of the second surface upon a detection of pixels of the EOI in the image of the first surface and in the image of the second image.

Stage 16 can include determining that the EOI has been exposed at the first and second surfaces, and stopping the milling of the first surface and the milling of the second surface.

FIG. 1 also illustrates configuration stage 15 that may be executed between stages 12 and 14. Stage 15 may facilitate the imaging of different surfaces of the object and of milling different surfaces of the object.

The configuration stage 15 can include adjusting ion optics (changing an angle of incidence), rotating (or otherwise moving) the object, moving a component of the system (thus changing the spatial relationship between the object and an ion miller) and the like.

Figure 2:
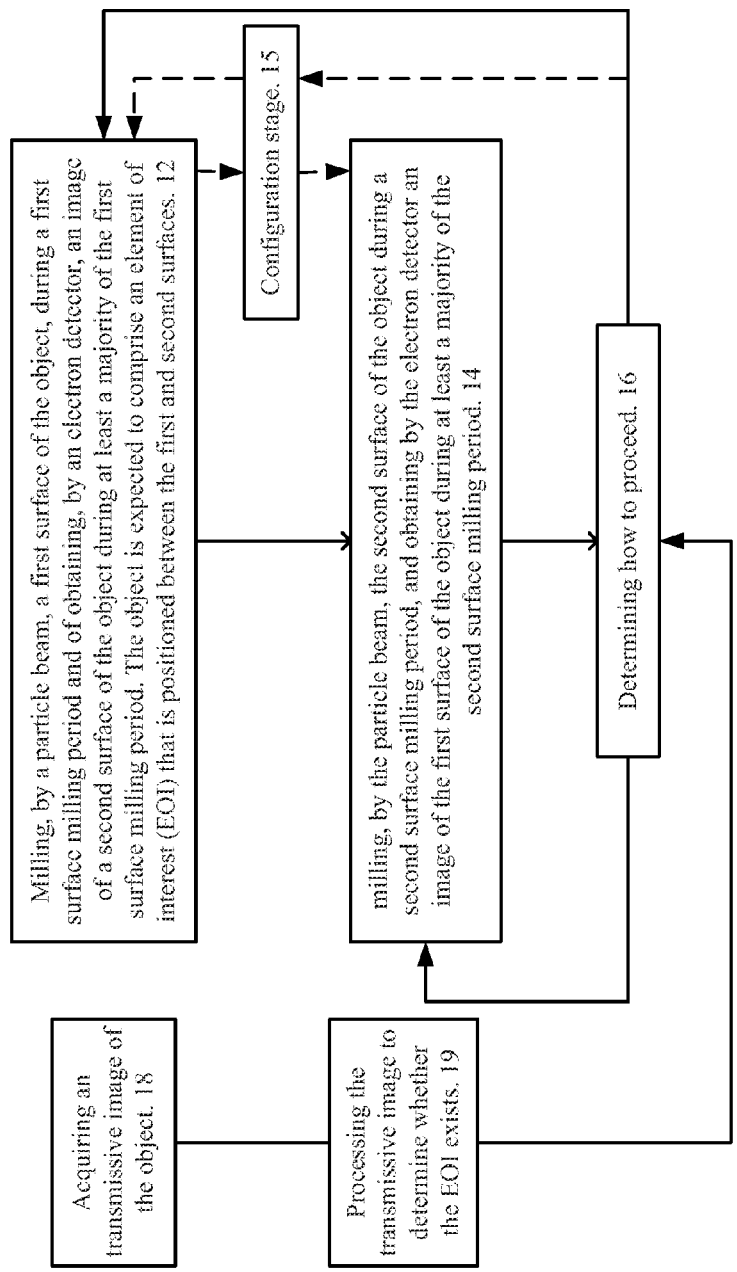
FIG. 2 illustrates a method according to an embodiment of the invention.

FIG. 2 illustrates a method 20 according to an embodiment of the invention.

Method 20 differs from method 10 by including a stage of validating the existence of the EOI within the object.

Method 20 may start by stage 12. Stage 12 may be followed by stage 14 (or by stage 15 that is followed by stage 14).

The determining of the existence of the EOI can be evaluated from the beginning of method 20 or when the distance between the first and second surfaces reaches a value that is expected to facilitate an acquisition of transmissive images of the object of acceptable quality. This distance may be set in advance, may be calculated given the expected transparency of the object and the EOI, or can be set based on previous measurements.

A transmissive image is obtained by electrons that pass through the object.

Method 20 may include stage 18 of acquiring a transmissive image of the object and stage 19 of processing the transmissive image to determine whether the EOI exists. Transmissive images that are of lower than acceptable quality or those that include not information (the object is not thin enough to allow the acquisition of transmissive images) can be ignored of.

Stage 19 can be followed by stage 16. If stage 19 determines that the object includes the EOI then the iterations of stages 12 and 14 can proceed—else the method ends.

FIGS. 3a-3c illustrates three examples of a cross section of object 111-113 that includes EOI 104 and images of such objects according to various embodiments of the invention. These are initial cross sections of the objects 111-113. It is assumed that in this initial condition transmissive images of the object of adequate quality can be obtained.

a. The cross section 31 of FIG. 3a illustrates object 111 that includes the EOI 504 near its upper surface.
    b. The cross section 32 of FIG. 3b illustrates object 112 that includes an EOI 504 at its center—far from its upper and lower surfaces.
    c. The cross section 33 of FIG. 3c illustrates object 113 that includes the EOI 504 near its lower surface.

FIG. 3d illustrates a target cross 34 section—the cross section of each of the objects 111-113 at the end of the milling process—a milled object in which the EOI 504 is exposed on both sides.

FIGS. 3e-3h illustrate images 141,142 and 143 of the upper surfaces of objects 111-113, images 151,152 and 153 of the lower surfaces of objects 111-113, and transmissive images 161, 162 and 163 of objects 111-113, as well as images 144, 154 and 164 of the upper surface of the milled object, the lower surface of the milled object and a transmissive image of the milled object.

FIGS. 4a-4f illustrate various timing diagrams 410, 420, 430, 440, 450 and 460 according to an embodiment of the invention.

Timing diagram 410 of FIG. 4a illustrates multiple iterations of a sequence that includes stages 14, 15 and 16. It is assumed that during a last iteration of the sequence the EOI is exposed on both sides and that the iterations can stop. It is further assumed that each image is obtained during the entire surface milling period. Boxes 414 represent first surface milling periods, boxes 416 represent second surface milling periods and dashed arrow 415 represent a duration of time gaps between the ending of one surface milling period and the start of another surface milling period.

The relationship between the duration of the time gap and each of the first and second surface milling period can exceed one, exceed three, exceed five, exceed eight, exceed ten and can even exceed higher values. In any case their durations exceed a long duration threshold.

FIG. 4a illustrates the duration of the first surface milling period as being equal to the duration of the second surface milling period but they can differ from each other.

Timing diagram 420 of FIG. 4b illustrates multiple iterations of a sequence that includes stages 14, 15 and 16. It is assumed that during a last iteration of the sequence the EOI is exposed on both sides and that the iterations can stop. It is further assumed that each image is obtained during the entire surface milling period. FIG. 4b differs from FIG. 4b by having first surface milling periods of unequal duration—the duration decreases during the end of the iterations.

Timing diagram 430 of FIG. 4c illustrates multiple iterations of a sequence that includes stages 14, 15 and 16. It is assumed that during a last iteration of the sequence the EOI is exposed on both sides and that the iterations can stop. It is further assumed that each image is obtained during a majority (about 80%) of the entire surface milling period—this is illustrated by dashed boxes 438 and 439 that represent the image acquisition periods.

Timing diagram 440 of FIG. 4d illustrates multiple iterations of a sequence that includes stages 14, 15 and 16. It is assumed that the EOI is exposed at the first surface before being exposed at the second surface—and the latter exposure requires multiple iterations of step 16—thus the process ends by multiple stages of step 16. It is further assumed that each image is obtained during the entire surface milling period. Boxes 414 represent first surface milling periods, boxes 416 represent second surface milling periods and arrows 415 represent the time gaps between the ending of one surface milling period and the start of another surface milling period.

Timing diagram 440 of FIG. 4e illustrates multiple iterations of a sequence that includes stages 14, 15 and 16. It is assumed that the EOI is exposed at the second surface before being exposed at the first surface—and the latter exposure requires one more iteration of step 14—thus the process ends by step 14. It is further assumed that each image is obtained during the entire surface milling period.

Boxes 414 represent first surface milling periods, boxes 416 represent second surface milling periods and arrows 415 represent the time gaps between the ending of one surface milling period and the start of another surface milling period.

Timing diagram 420 of FIG. 4f illustrates multiple iterations of a sequence that includes stages 14, 15 and 16. It is assumed that during a last iteration of the sequence the EOI is exposed on both sides and that the iterations can stop. It is further assumed that each image is obtained during the entire surface milling period. FIG. 4f differs from FIG. 4a by having first surface milling periods that differ by duration from the second surface milling periods.

Figure 5:
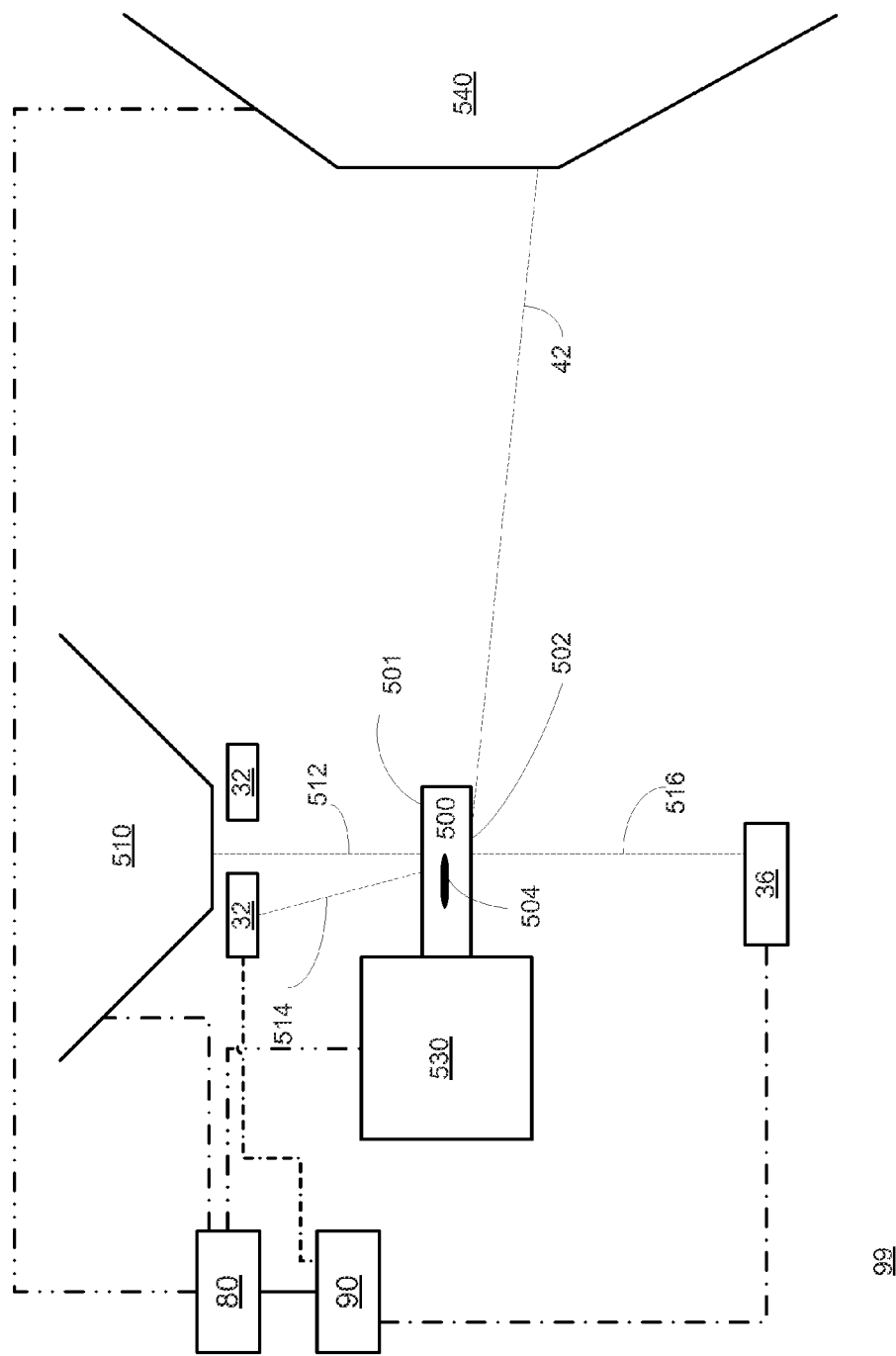
FIG. 5 illustrates a system and an object according to an embodiment of the invention.

FIG. 5 illustrates a system 99 for imaging and milling an object 500, according to an embodiment of the invention.

Object 500 may be, for example, a wafer, an electronic circuit, or any other object that may be processed by a charged particle beam such as an electron beam, an ion beam, or any other type of electronically charged particles processing.

Object 500 may conveniently be positioned on a stage or other support structure 100(8), which may move the object in one or more directions—e.g. moving in the X, Y and/or Z axes, and/or rotating around one or more of those axes. Object 500 may be held against a stage, placed on it, or otherwise detachably attached to it. The support structure can be a manipulator or a part of a manipulator.

System 99 may include controller 80, an ion miller 540, an image processor 90, and least one electron detector such as the first electron detector 32 that is positioned near a first column 510 of a first scanning electron microscope (SEM). System 99 may also include a transmissive electron microscopy (TEM) detector 36.

First column 510 is illustrated as generating a primary electron beam 512 that is directed towards the first surface 501 of the object. Some of the electrons that are scattered from the first surface 501 are represented by line 514 and are detected by the first electron detector 32. Electrons that pass through the object are represented as dashed arrow 513 that is detected by the TEM detector 36.

The ion miller 540 can generate a charged particle beam such as ion beam 42 that can mill the object 500.

FIG. 5 illustrates the ion beam 42 as milling a second surface 502 of the object while the SEM generates (by utilizing the first electron detector 32) an image of the first surface 501 of the object 500. Object 500 includes element of interest (EOI) 504 that is located between the first and second surfaces 501 and 502.

Figure 6:
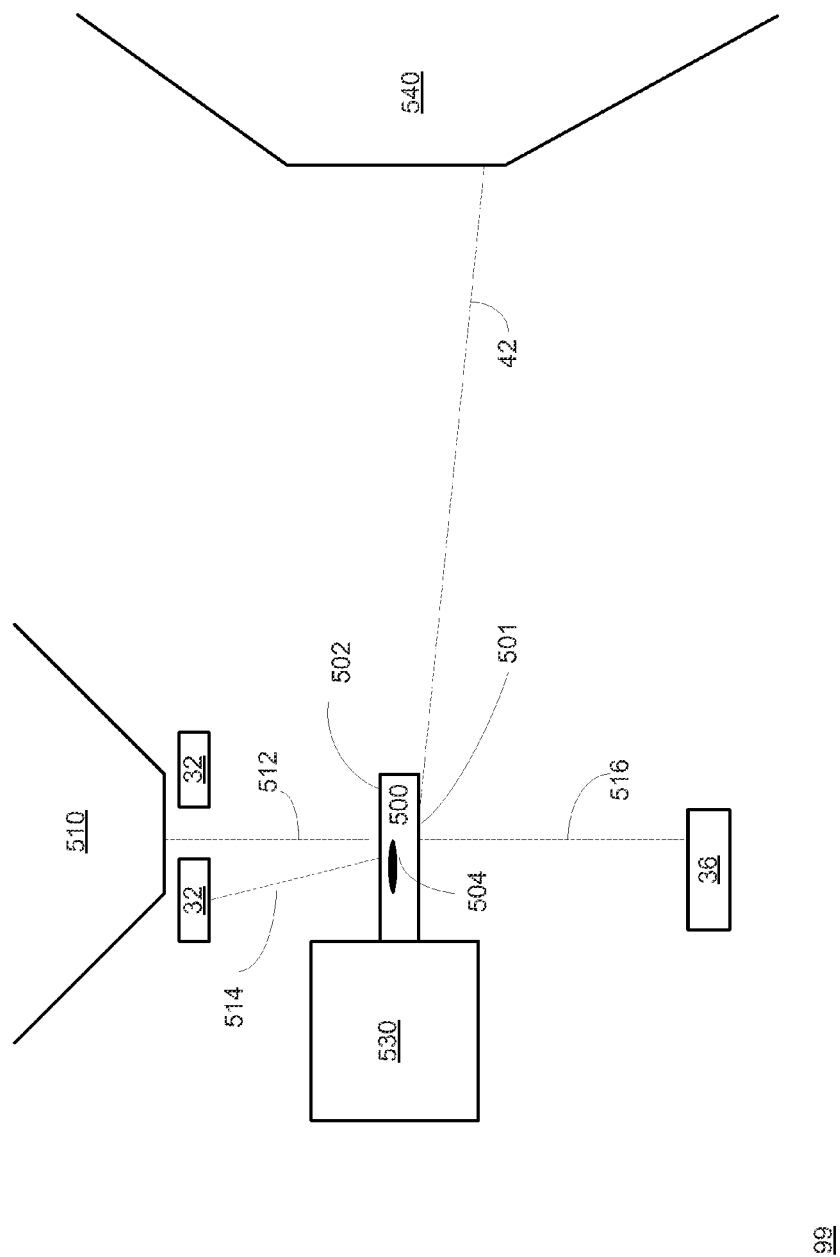
FIG. 6 illustrates a system and an object according to an embodiment of the invention.

FIG. 6 illustrates the ion beam 42 as milling the first surface 501 of the object while the SEM generates (by utilizing the first electron detector 32) an image of the second surface 502 of the object 500.

The system 99 can perform multiple repetitions of the milling and images stages (12, 14) illustrated in FIGS. 1 and 2.

Accordingly, the system 99 may be arranged to perform at least one iteration of a sequence that includes:
  milling, by a particle beam from the ion miller, a first surface of the object, during a first surface milling period and obtaining, by the electron detector, an image of a second surface of the object during at least a majority of the first surface milling period; and
  Milling, by the particle beam, the second surface of the object during a second surface milling period, and obtaining by the electron detector an image of the first surface of the object during at least a majority of the second surface milling period.

The controller 80 can be arranged to perform at least one of the following stages:
  a. Stop the milling of the first surface and the milling of the second surface upon a detection, by the image processor, of pixels of the EOI in the image of the first surface and in the image of the second image.
  b. Determine that the EOI has been exposed at the first and second surfaces; and to stop the milling of the first surface and the milling of the second surface.

Figure 11B:
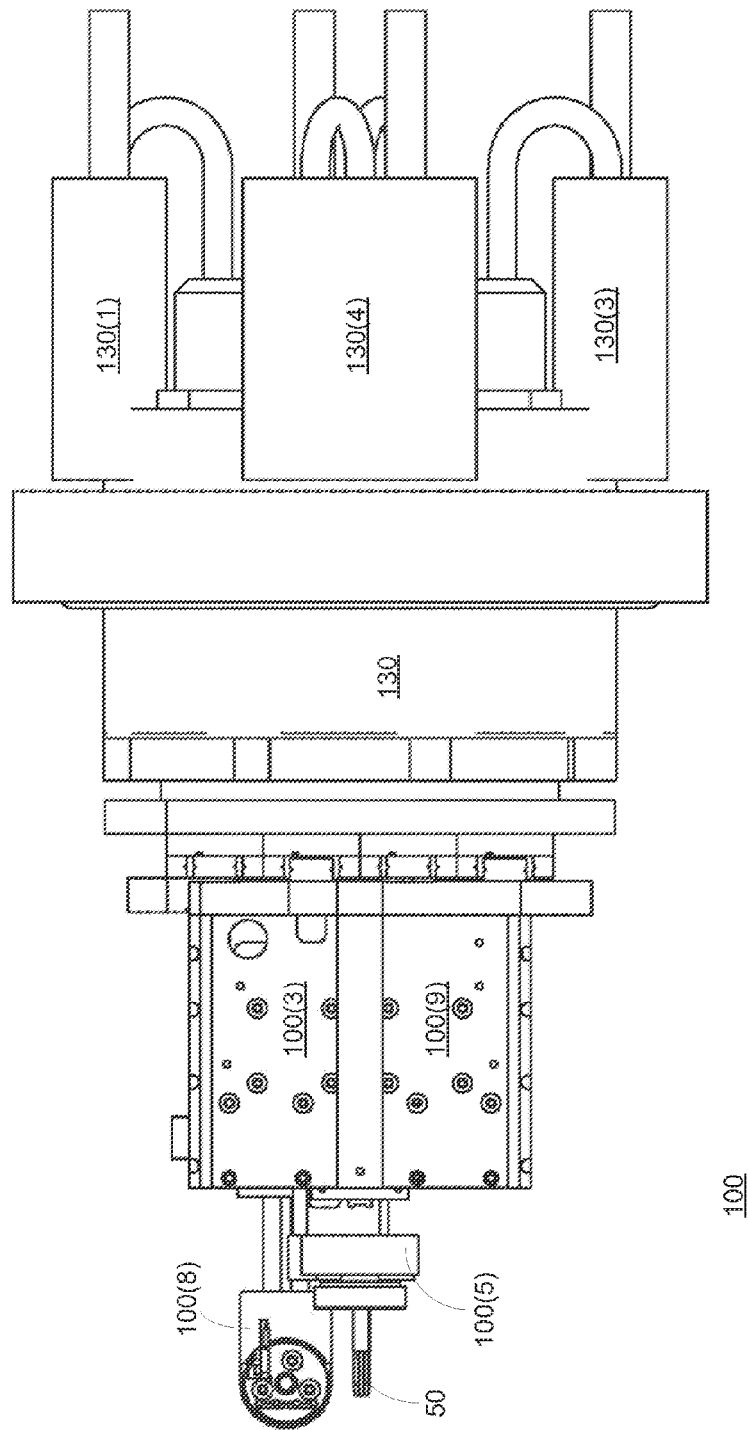
Figure 11C:
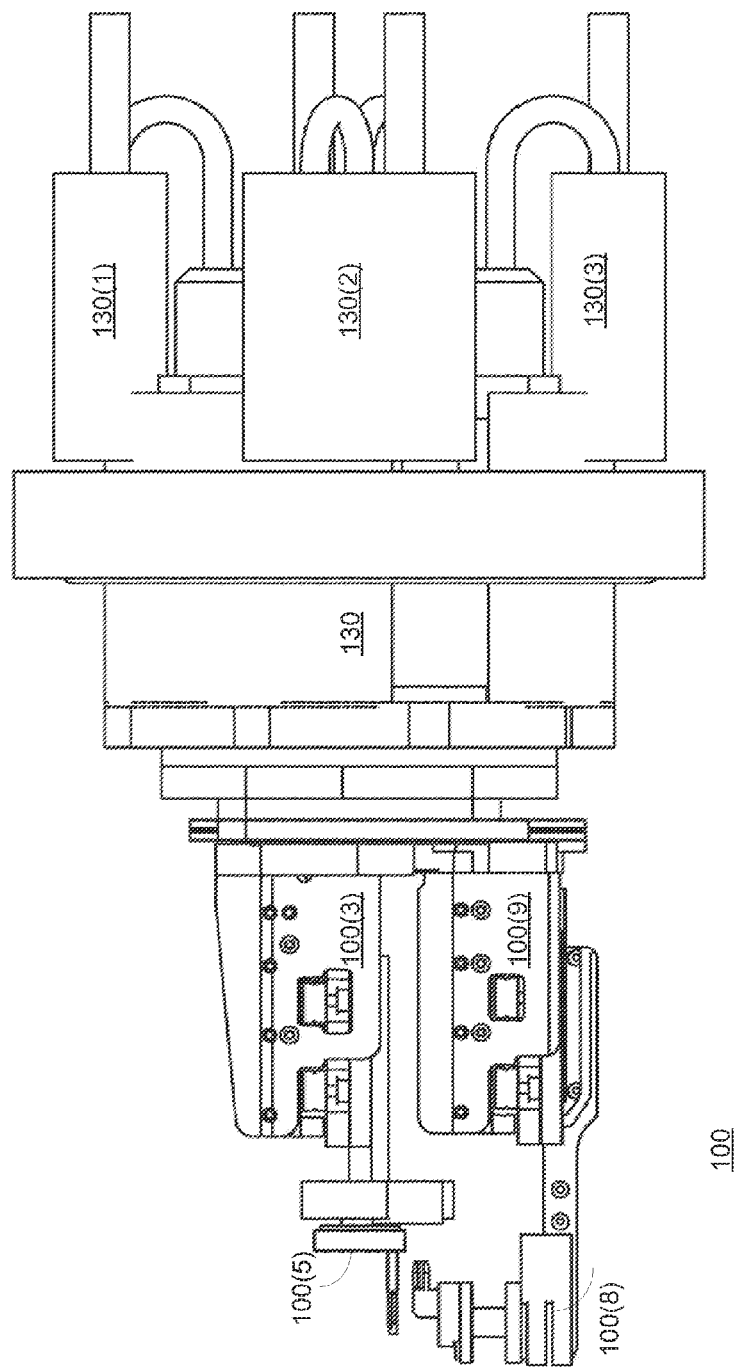

The system 99 may include a mechanical element such as supporting element 100(8) or a manipulator (such as manipulator 100 of FIGS. 11A-11C). The manipulator may include supporting element 100(8).

The mechanical element can be arranged to change a spatial relationship between the object and the changed particle device between the milling of the first surface of the object and milling the second surface of the object.

The TEM detector 36 can send detection signals that may be processed by the image processor 90 to provide a transmissive image of the object 500.

The controller 80 can be arranged to determine, based on the transmissive image of the object 500, whether the object includes the EOI and to stop an execution of the sequence of the first and second surfaces if the controller determines that the object does not comprise the EOI.

The controller 80 can be arranged to determine whether the object 500 includes the POI only after the transmissive image of the object exhibits a predetermined signal to noise ratio.

It is noted that each one of the first and second surfaces 501 and 502 can be milled while each one of the second and first surfaces 502 and 502 may be imaged without changing the spatial relationship between the object and various components of the system.

Figure 7:
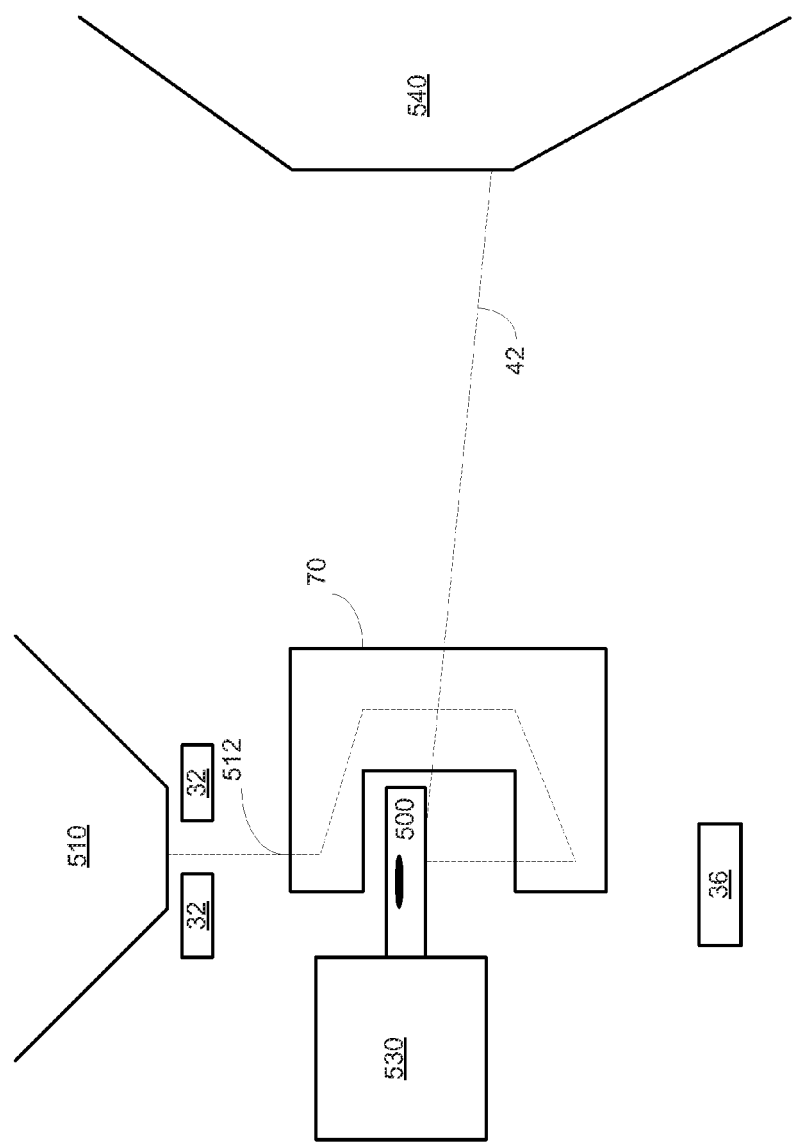
FIG. 7 illustrates a system and an object according to an embodiment of the invention.

FIG. 7 illustrates system 97 according to an embodiment of the invention. System 97 includes electron optics 70 that may direct the primary beam 512 from column 500 (positioned above the first surface 501 of the object 500) towards the second surface 502 of the object so that the primary beam 512 impinges on the second surface 502 of object 500—while the ion beam 84 mills the first surface 501 of the object 500.

TEM detector 36 can serve as an electron detector for detecting electrons reflected or scattered from the second surface 502. Additionally or alternatively, system 97 may include one or more electron detectors (now shown) for detecting electrons scattered and/or reflected from the second surface 502 of the object 500.

Electron detectors 32 can serve as TEM detectors. Additionally or alternatively, the system 97 may include an additional TEM detector (not shown).

The electron optics may be ignored when the system 97 images the first surface 501 of the object 500.

Figure 8:
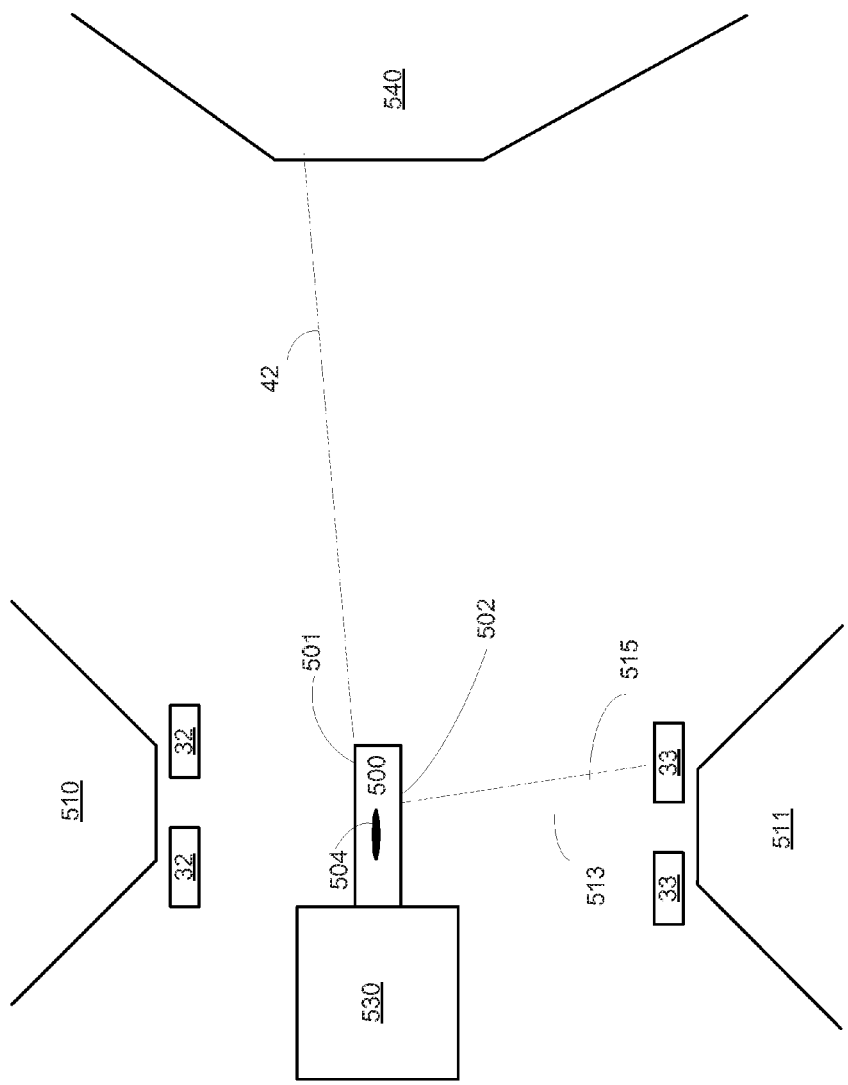
FIG. 8 illustrates a system and an object according to an embodiment of the invention.

FIG. 8 illustrates system 98 according to an embodiment of the invention. System 98 includes two SEMs. A first SEM includes first column and a second SEM includes second column 511. These columns are positioned on opposite sides of the object 500.

Column 510 obtains images (non-transmissive) of the first surface 501 of the object while the ion beam 84 mills the second surface 502 of the object.

Column 511 obtains images (non-transmissive) of the second surface 502 of the object while the ion beam 84 mills the first surface 501 of the object.

FIG. 8 illustrates a primary electron beam 513 of column 511 and detection (dashed line 515) of scattered electrons by electron detector 33.

It is noted that system 98 may have dedicated TEM detectors. Additionally or alternatively, one or more electron detectors such as 32 and 33 can be used as a TEM detector while one or more electron detectors of the other SEM are used for detecting secondary electrons.

FIG. 9 illustrate a detailed cross section of a system 91 according to an embodiment of the invention.

The system 91 includes: (a) an ion miller 540 that include deflector 910, (b) a SEM that includes a column 510 and one or more detectors, (c) a manipulator 100(8) that holds the object 500 and one or more electron detectors such as (a) a first secondary electron detector 551 that is located between the SEM column 510 and the object 500, (b) a second secondary electron detector 552 and (c) a transmissive (TE) electron detector 553. The detectors 552 and 553 are positioned at the same side of the object 500. The object 500 is positioned between the SEM column 510 and detectors 552 and 553.

Figure 13:
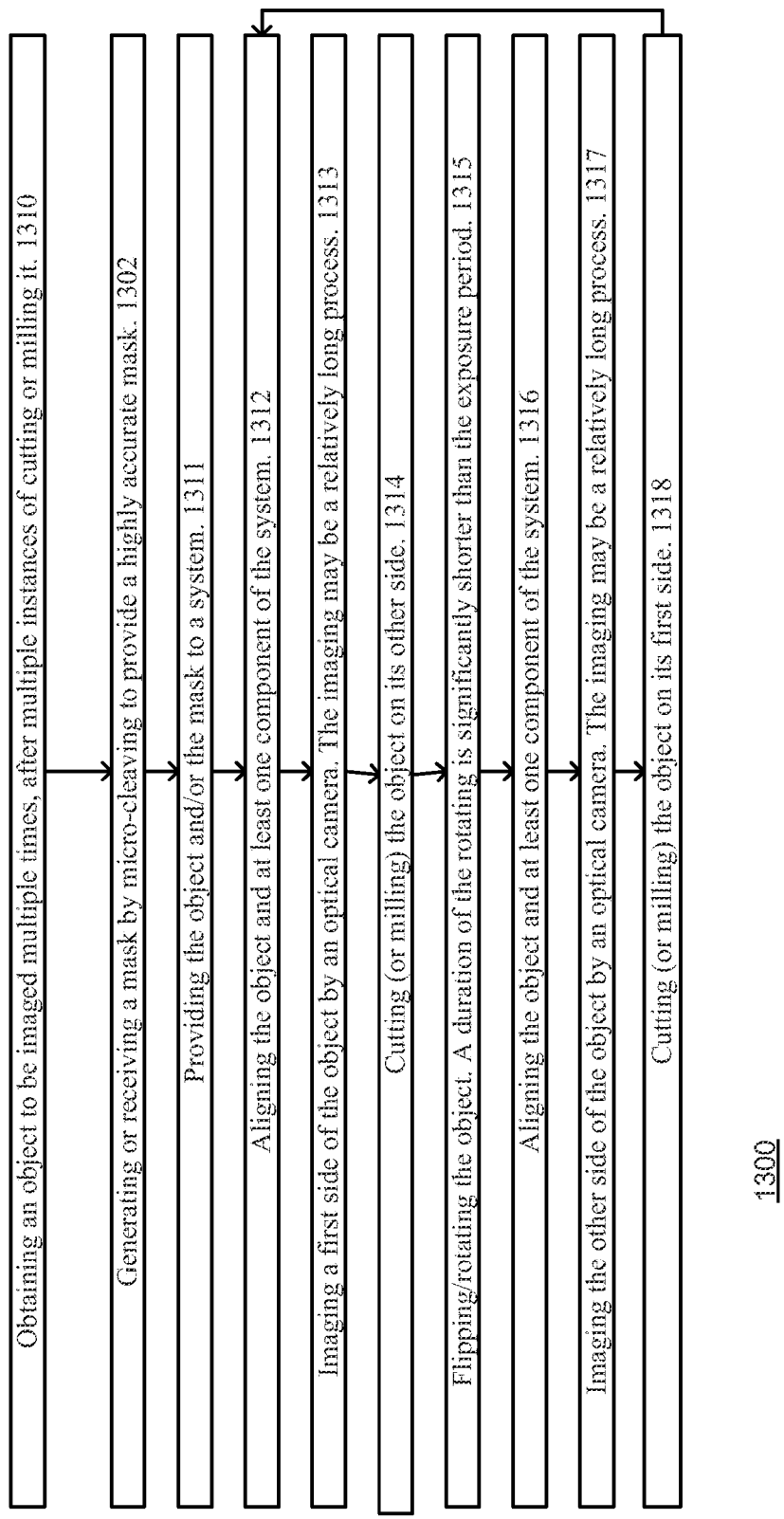
FIG. 13 illustrates a method according to an embodiment of the invention.

System 91 can apply any of the methods illustrated in FIGS. 1, 2 and 13.

The system may include a secondary detector 552 that detects secondary electrons that propagate along directions that differ from the direction of the beam that passes through the sample—it may include an aperture for allowing a transmissive detector 553 to detect electrons that propagate along a path that coincides with the path of the primary electron beam.

Figure 10A:
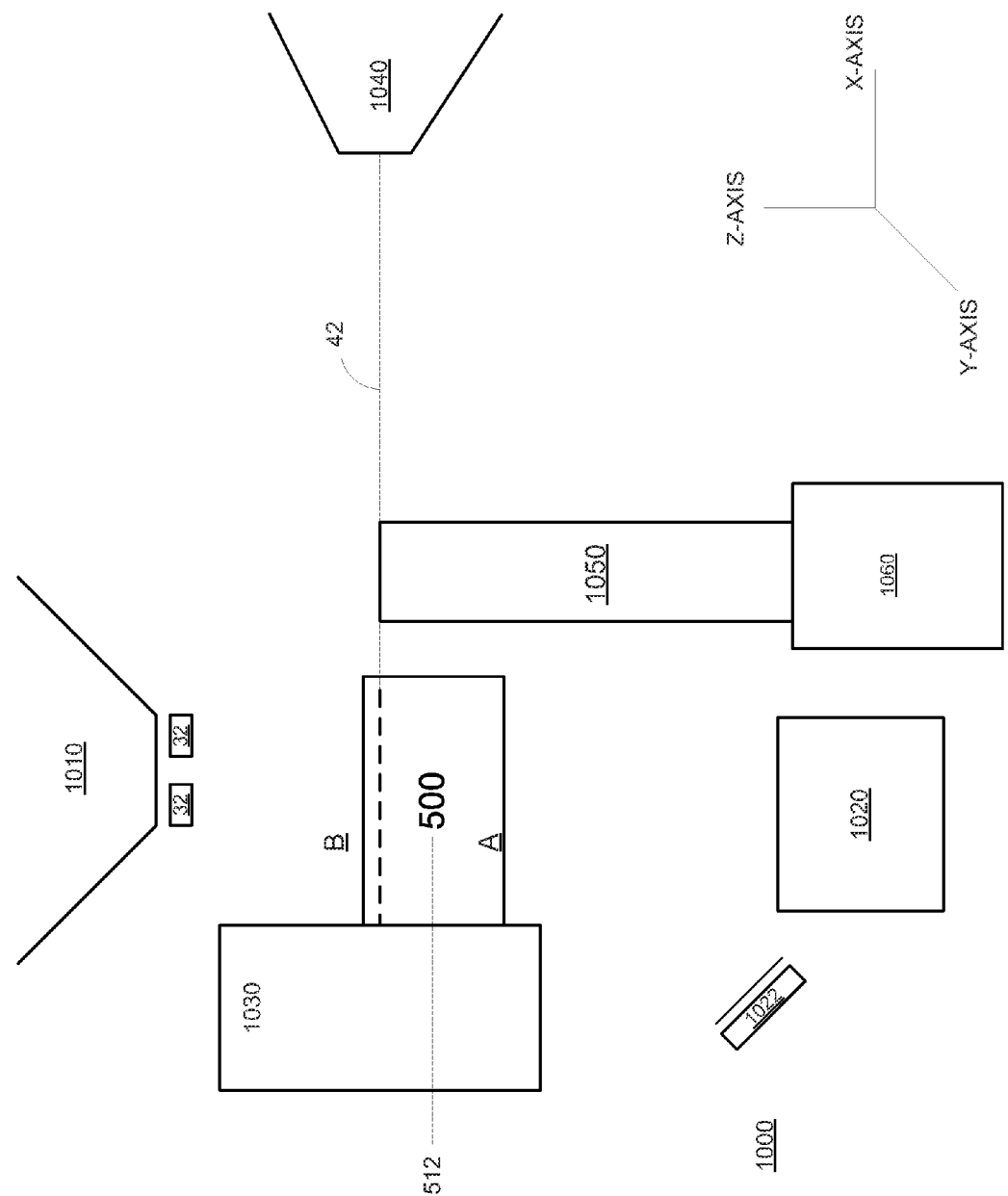

FIG. 10A illustrates a system 1000 according to an embodiment of the invention. The system 1000 is shown as including an image acquisition unit 1020 that is adapted to image object 500 from a first direction (denoted "A"). The image acquisition unit 1020 can image a first surface 101 of the object. It is noted that image acquisition unit 1020 be an optical unit and may be adapted to image object 500 from a first direction (denoted "A"). The image acquisition unit 1020 can image a first surface 101 of the object. The image acquisition unit 1020 may include an optical image acquisition unit that is capable to acquire light reflected from object 500 and to image it accordingly, but other types of image acquisition units may also be implemented.

It is noted that many types of image acquiring techniques (including but not limited scanning electron microscopy SEM images) may require relatively long exposure duration, in which the image acquiring system is exposed to a charged particles (light, or other forms of radiation) from the imaged object. For example, in some industries, exposure durations (or acquisition durations) may be as long as 10 second, 30 seconds, 1 minute, 10 minutes, and even longer.

System 1000 further includes an ion miller 1040, or other unit capable of milling and/or cutting portions of object 500 using electrically charged particles (e.g. electrons, ions). The ion miller 1040 is conveniently configured to cut-off portions of object 500, from a side of object 500 that is different than the first direction, and potentially opposite to it (such a side is denoted "B").

The milling and/or cutting may be made through or otherwise using a mask 1050. it is noted that, according to an embodiment of the invention, the system 10 may generate or receive a mask 1050 by micro-cleaving to provide a highly accurate mask. If the system generates the mask 1050 then it may includes a micro-cleaving unit (not shown). Mask 1050 may be held by an angular stage 1060.

It is noted that it is usually undesirable to stop an operation of the milling process by ion miller 1040 for the duration it requires to image, especially as stopping of the operation of the ion miller may result various problems. In the proposed system, the milling may be carried out on side B, while an image of side A is acquired.

According to an embodiment of the invention, a processor of system 1000 (not illustrated) may be configured to time milling of side B of object 500 according to a duration period of side A, and/or to set an exposure period of side A according to a milling period on side B.

According to an embodiment of the invention, system 1000 is capable of rotating object 500, e.g. so as to flip sides of object 500. This may be implemented, for example, by a rotating stage 1030, but this is not necessarily so. The rotating may be rotating across axis 512.

After object 500 has been rotated, the side that has been milled now faces the image acquisition unit, while the opposite side—which has been imaged—is not ready to be cut by ion miller 1040.

It is noted that mechanical movement—which either result from the flipping/rotating of the object 500, or from another mechanical movement in system 1000, may require an aligning of object 500 before another sequence of milling, cutting, and/or imaging can be carried out. Therefore, according to an embodiment of the invention, system 1000 may include an alignment unit 1010 for aligning object 500.

According to an embodiment of the invention, system 1000 may include detector 32 and/or 34 used to monitor an alignment process between the object 500 and the mask 1050, or between object 500 and another one or more component of system 1000. The alignment process may include aligning the mask 1050 and object 500 so that they are parallel to each other (both can be horizontal) or be positioned on any other manner) and the edge of the mask 1050 is positioned directly above an imaginary line 42 that represents a desired milled edge of object 500 after being milled during a first milling sequence.

This imaginary line can be located few nanometers from a center of the object 500, few nanometers from an edge of object 500, or in other locations.

Figure 10C:
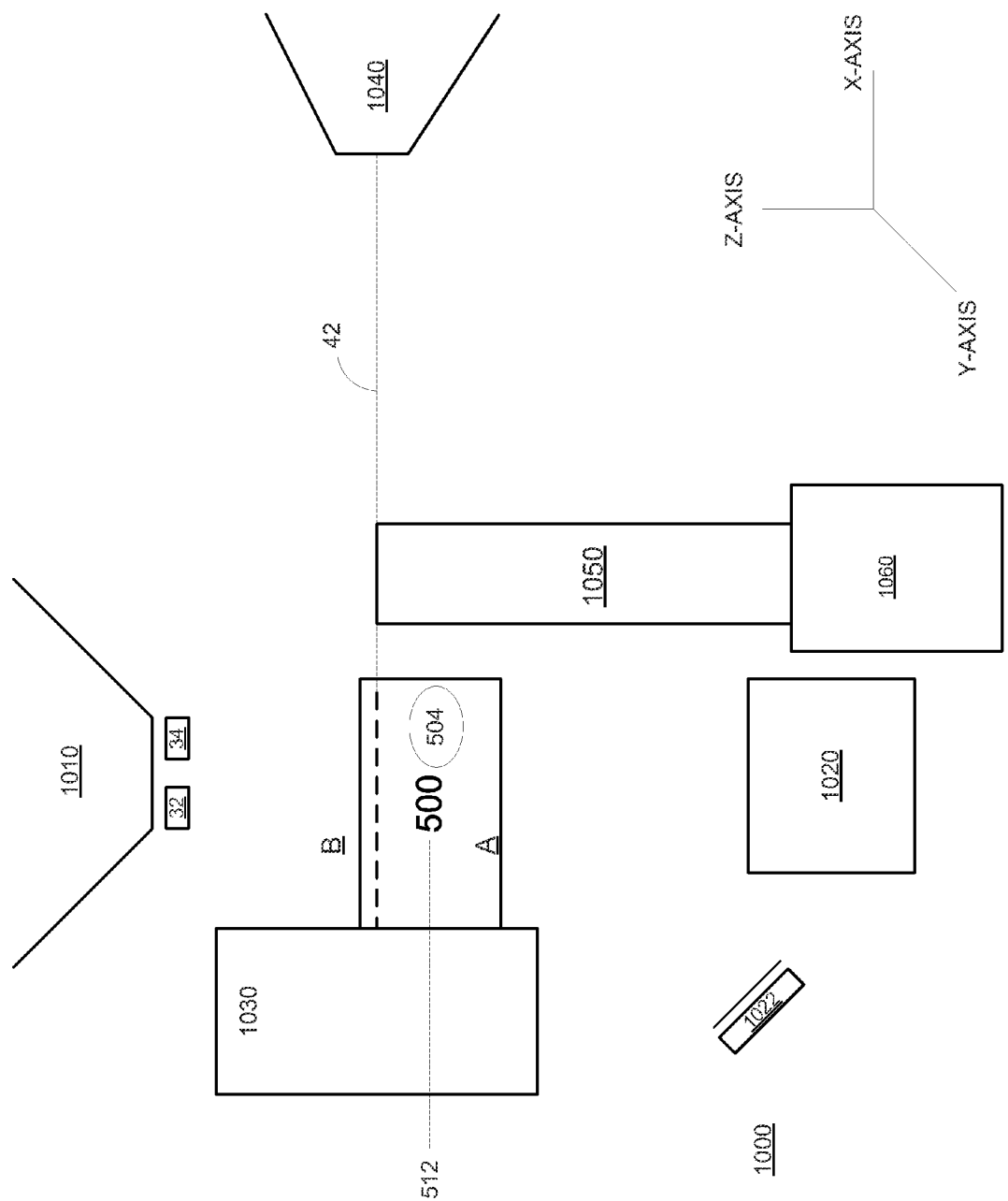

According to an embodiment of the invention, the alignment process may be made when the mask and the sample are rotated with respect to what is shown in FIGS. 10A and 10C. Such a configuration is illustrated in FIG. 10B.

According to an embodiment of the invention, once the alignment process ends the mask 1050 and object 500 are rotated (e.g. by a main rotating stage) about an axis, while maintaining the alignment so that the mask 1050 and object 500 face the ion miller 1040.

According to an embodiment of the invention, the ion miller 1040 performs a first milling sequence that includes milling the exposed portion of the edge of object 500 by a dual deflection while observing the milling by the scanning electron microscope (e.g. using detectors 32 and/or 34), the milling thins the edge of object 500 on one side to provide a milled side of a partially milled object 500. The ion beam 42 can be deflected within the X-Y plane, but this is not necessarily so.

After one side of the object 500 is milled, spatial relationship between the mask 1050 and the partially milled object 500 may be changed in order to expose the other side of object 500 to the ion miller 1040. This may include rotating the partially milled object 500 about its axis (512) by the stage 1030, and may also include changing the height of the mask 50.

After the spatial relationship is changed, the ion miller 1040 performs a second milling sequence (see, for example, FIG. 100) that includes milling the other (now exposed) edge of the partially object 500 while observing the milling by the scanning electron microscope and (optionally—when the partially milled sample starts to be partially transparent to electrons) by a TEM or an STEM detector.

This process may be reiterated until reaching a desired condition.

It is noted that the number of detectors, their location, the types of detectors and the number of parts of each detector (as well as their size and shape) can differ from the example illustrated above.

Referring to FIG. 10B, it is noted that, according to an embodiment of the invention, object 500 may include one or more areas 101 that should not be cut or milled. Therefore, according to an embodiment of the invention, system 1000 may prevent cutting of such areas 101 by ion miller 1040. This may require monitoring by image acquisition unit 1020 (also referred to as camera 1020), and/or by other imaging unit such as one of alignment unit 1010. It is noted that the area 101 (which may also be defined volumetrically) may be defined either by characteristics or by its location.

According to an embodiment of the invention, when the milling from at least one of the sides becomes closer to the protected area 101, a processor of system 1000 may determine to use shorter milling/cutting intervals (e.g. 15 second instead of 30 seconds) in order to prevent undesired cutting of substantial portions of area 101, and as a result to acquisition time of camera 1020 may also be reduced—which may result in acquiring images of lower quality.

Figure 11D:
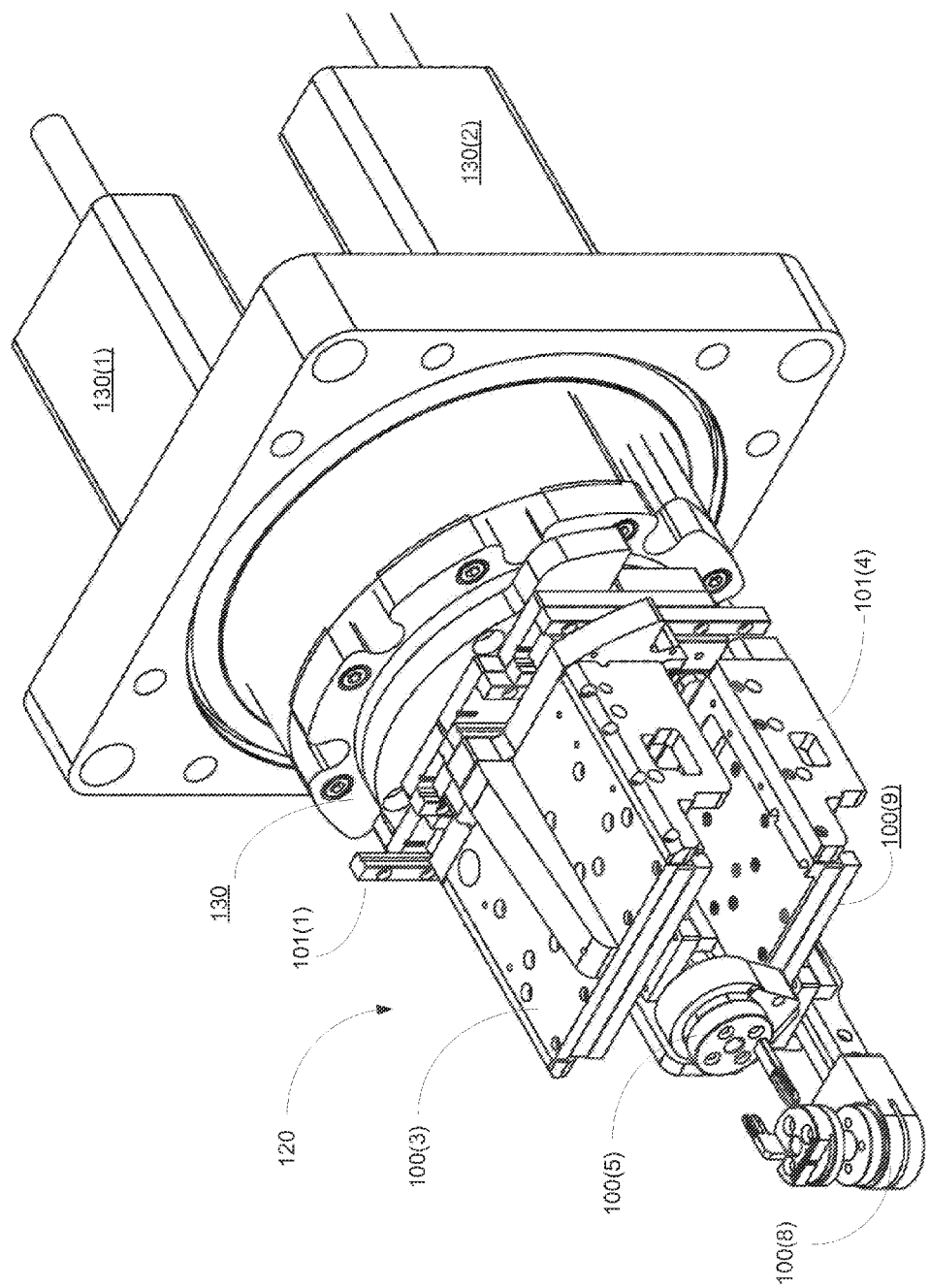

FIGS. 11A-11C illustrate a manipulator 100 according to various embodiment of the invention. FIG. 11A is a front view of the manipulator 100, FIG. 11B is a top view of the manipulator 100, FIG. 11C is a side view of the manipulator 100 and FIG. 11D is a three-dimensional view of the manipulator 100, all according to an embodiment of the invention.

The manipulator 100 includes two separate subunits 110 and 120 both located on a main rotating stage 130. The rotating stage 130 is separated by and powered by engines 130(1)-130(4).

The second subunit 120 may manipulate the sample and the mask and may have X, Y, Z and θ stages. In FIG. 6 these stages are denoted as follows: X-stage 100(1), Y-stage 100(2), Z-stage 100(3) and θ stage 100(5).

The first subunit 110 may manipulate the sample—it may change the spatial relationship between the mask and the sample—for example by moving the mask in relation to any movement introduced by the second sub-unit 120. It is noted that each of the mask and sample can be moved by subunits—each can move in relation to each other and not share stages such as rotating stage 130.

The first subunit 110 may have X, Y, Z and θ stages. In either one of FIGS. 6 and 9 these stages are denoted as follows: X-stage 100(11), Y-stage (not shown), Z-stage 100(9), and θ stage 100(8).

The second subunit 120 may manipulates the mask and may also manipulate technological accessories such as mask, calibrating plate, apertures, target for deposition etc.

The first subunit 110 may receive the sample or technological accessories from a sample holder (also referred to as shuttle 103). The shuttle 103 may be transferred until it is positioned on the sample angular stage 100(8).

The stages are connected between structural elements such as plates, beams, rails, guidelines and the like denoted 101(1)-101(5).

Figure 12:
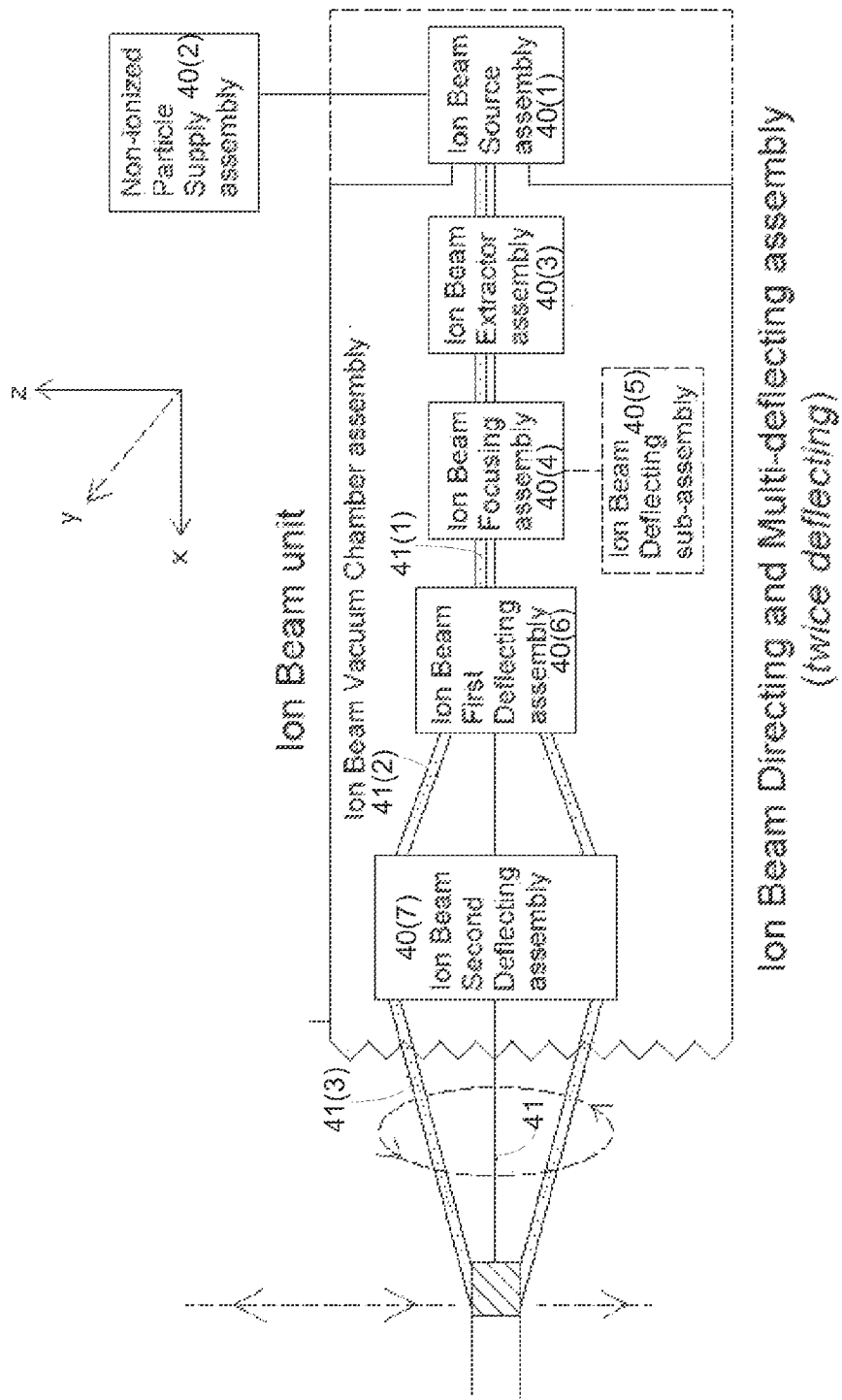
FIG. 12 illustrates a portion of a system and an object according to an embodiment of the invention.

Referring to FIG. 12, the ion miller 540 (also referred to as ion sputtering system) can have the following capabilities and degrees of freedom:
a. Wide range of ion energy control to allow quick bulk removal to intensify the process as well as gentle milling mode to provide highest level of the final quality of a treated sample.
b. High ion current density for short process duration.
c. Control of ion current uniformity along beam cross section to provide uniform treatment of a sample.
d. Variable incidence angle of the beam relatively to the sample surface to avoid selective milling of the sample surface.
e. Control of the beam shape and size to provide variety of applications and technological modes.
f. Beam pulsating for uniformity of sample treatment.
g. Beam accurate positioning to provide specific area of a sample treatment.
h. Beam scanning in orthogonal directions for uniformity of sample treatment.
i. Eu-centric beam rotation around area of interest for uniformity of sample treatment.

The ion miller 540 may include:
a. Duo-plasmatron ion source to ignite the plasma.
b. Beam formation module to extract and collect Xe+ ion beam from the plasma.
c. Final optics to focus and direct ion beam toward a treated sample.
d. Xe gas supply system to provide an automatic gas delivery of constant and specified pressure.
e. Leak-valve that provides automatic supply of metering amount of the gas into the ion source for plasma ignition and ion beam formation.
f. Electronics and power supplies to provide automatic control of the ion sputtering system.

FIG. 12 illustrates the ion miller 540 as including an ion beam source assembly 40(1), a non-ionized particle supply assembly 40(2), an ion beam extractor assembly 40(3), an ion beam focusing assembly 40(4), an ion beam deflecting subassembly 40(5), an ion beam first deflecting assembly 40(6), and an ion beam second deflecting assembly 40(7).

The ion beam source assembly 40(1) is fed by the non-ionized particle supply assembly 40(2) and the ion beam extractor assembly 40(3) outputs an ion beam that propagates along an optical axis 41 of the ion miller. The ion beam focusing assembly 40(4) focuses the ion beam and feeds the focused ion beam to ion beam first deflecting assembly 40(6) that rotates the ion beam and directs it along directions that are spaced apart from the optical axis of the ion miller to provide deflected and rotated ion beam 41(2). The ion beam second deflecting assembly 40(7) directs the rotating ion beam towards the optical axis, while maintaining the rotation of the ion beam 41(3). The rotation constantly changes milling angle and provide a smoother milled sample.

A non limiting example of an ion miller is provided in US patent application publication serial number 2008/0078750A1 titled "Directed Multi-Deflected Ion Beam Milling of a Work Piece and Determining and Controlling Extent Thereof", which is incorporated herein by reference.

According to an embodiment of the invention, a method for imaging is disclosed. This method may be implemented, for example, by a system such as system 1000. FIG. 13 illustrates method 1300 according to an embodiment of the invention.

The method may start with generating or receiving (1302) a mask by micro-cleaving to provide a highly accurate mask. An example for micro-cleaving is illustrated in U.S. Pat. No. 6,223,961 titled "Apparatus for cleaving crystals", which is incorporated herein by reference.

The method includes obtaining (1310) an object to be imaged multiple times, after multiple instances of cutting or milling it.

Stage 1310 may include providing (1311) the object and/or the mask to a system such as system 1000.

Stage 1311 may continue with aligning (1312) the object and at least one component of the system. This may be done using a moving stage and at least one out of a scanning electron microscope and an optical microscope.

The aligning (1312) may be followed by imaging (1313) a first side of the object by an optical camera. The imaging may be a relatively long process.

The method further includes cutting (or milling) (1314) the object on its other side. It is noted that the cutting may be carried out at least partly concurrently to the imaging, and according to an embodiment of the invention, more than a half of the exposure period of the camera overlaps a cutting period. According to an embodiment of the invention, those periods overlap each other by over 95% (and even by over 99%).

The method continues by flipping/rotating (1315) the object, wherein a duration of the rotating is significantly shorter than the exposure period (e.g. less than 10% of it, and even less than 2% of it).

The rotating is followed by another instance of imaging (1317) and cutting (1318), carried out on the opposite sides of the object this time. This other instance may be preceded by another stage of aligning (1316).

Such iterations of flipping, imaging and cutting may be reiterated multiple times, wherein in each time another side of the object is being cut, and the opposite side is being imaged. It is noted that some of the instances may be of same duration, but this is not necessarily so.

The present invention can be practiced by employing conventional tools, methodology and components. Accordingly, the details of such tools, component and methodology are not set forth herein in detail. In the previous descriptions, numerous specific details are set forth, in order to provide a thorough understanding of the present invention. However, it should be recognized that the present invention might be practiced without resorting to the details specifically set forth.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

We claim:

1. A method for milling and inspecting an object, the method comprises:
performing by a system that comprises a controller, an ion miller, an image processor and a first electron detector at least one iteration of a sequence that comprises:
milling, by a particle beam from the ion miller, a first surface of the object, during a first surface milling period;
obtaining, by the first electron detector, an image of a second surface of the object during at least a majority of the first surface milling period; wherein the object is expected to comprise an element of interest (EOI) that is positioned between the first and second surfaces;
milling, by the particle beam, the second surface of the object during a second surface milling period;
wherein each of the first surface milling period and the second surface milling period has a duration that exceeds 0.1 seconds;
obtaining by the first electron detector an image of the first surface of the object during at least a majority of the second surface milling period.

2. The method according to claim 1, comprising stopping the milling of the first surface and the milling of the second surface upon a detection of pixels of the EOI in the image of the first surface and in the image of the second surface.

3. The method according to claim 1, comprising determining that the EOI has been exposed at the first and second surfaces; and stopping the milling of the first surface and the milling of the second surface.

4. The method according to claim 1, comprising performing multiple iterations of the sequence; wherein a length of at least one of the first and surface milling periods decreases with an expected decrement in a distance between the first and second surfaces.

5. The method according to claim 1, comprising performing multiple iterations of the sequence, wherein an energy of the particle beam reduces with an expected decrement in a distance between the first and second surfaces.

6. The method according to claim 1, wherein the particle beam is generated by an ion miller; wherein the method comprises changing a spatial relationship between the object and the ion miller between the milling of the first surface of the object and milling the second surface of the object.

7. The method according to claim 1, wherein the duration exceeds 1 second.

8. The method according to claim 1, wherein the duration exceeds 2 seconds.

9. The method according to claim 1, wherein the duration exceeds 3 second.

10. The method according to claim 1, wherein a duration of each of the first and second surface milling periods exceeds a time gap between an end of a first surface milling period and a start of a second surface milling period.

11. The method according to claim 1, wherein a duration of each of the first and second surface milling period is at least ten times a time gap between an end of a first surface milling period and a start of a second surface milling period.

12. The method according to claim 1, further comprising obtaining a transmissive image of the object by a transmissive image detector of the system, determining, based on a transmissive image of the object, whether the object comprises the EOI and stopping an execution of the sequence of the first and second surfaces if determining that the object does not comprise the EOI.

13. The method according to claim 12, comprising determining whether the object comprises the EOI only after the transmissive image of the object exhibits a predetermined signal to noise ratio.

* * * * *